United States Patent [19]

Baranyi et al.

[11] Patent Number: 4,524,218

[45] Date of Patent: Jun. 18, 1985

[54] PROCESSES FOR THE PREPARATION OF SQUARAINE COMPOSITIONS

[75] Inventors: Giuseppa Baranyi; Peter M. Kazmaier; Cheng-Kuo Hsiao; Richard A. Burt, all of Mississauga, Canada

[73] Assignee: Xerox Corporation, Stamford, Conn.

[21] Appl. No.: 570,563

[22] Filed: Jan. 11, 1984

[51] Int. Cl.$^3$ .................. C07C 85/00; C07C 85/02; C07C 85/06

[52] U.S. Cl. .................................................. 564/307

[58] Field of Search ........................................ 564/307

[56] References Cited

U.S. PATENT DOCUMENTS

| | | | |
|---|---|---|---|
| 3,617,270 | 11/1971 | Kampler et al. ................ | 96/1.7 |
| 3,824,099 | 7/1974 | Champ et al. .................. | 96/1.5 |
| 4,150,987 | 4/1979 | Anderson et al. ............... | 96/1.5 R |
| 4,311,573 | 1/1982 | Mayhan et al. ................ | 204/159.15 |
| 4,353,971 | 10/1982 | Chang et al. ................... | 430/58 |
| 4,390,610 | 6/1983 | Bowden et al. ................. | 430/58 |
| 4,391,888 | 7/1983 | Chang et al. ................... | 430/57 |
| 4,410,616 | 10/1983 | Griffiths et al. ................ | 430/59 |

OTHER PUBLICATIONS

White et al., "J.A.C.S.", 86, pp. 453–458, 2/1964.

*Primary Examiner*—Paul F. Shaver
*Attorney, Agent, or Firm*—E. O. Palazzo

[57] ABSTRACT

Disclosed is an improved process for the preparation of squaraine compositions which comprises reacting squaric acid, an aromatic amine, and a composition selected from the group consisting of phenols and phenol squaraines, in the presence of an aliphatic alcohol, and an optional azeotropic substance.

26 Claims, No Drawings

PROCESSES FOR THE PREPARATION OF SQUARAINE COMPOSITIONS

BACKGROUND OF THE INVENTION

This invention relates generally to improved processes for preparing squaraine compositions, and more specifically, the present invention is directed to processes for obtaining squaraine compositions of enhanced photosensitivity by accomplishing the reaction involved in the presence of phenols or phenol squaraines. In one embodiment of the present invention there is provided certain known squaraine compositions of enhanced photosensitivity by the reaction of squaric and an aromatic amine in the presence of a phenol or a phenol squaraine, followed by regenerating the crystallized mixture of squaraines by for example known evaporation techniques. The squaraine compositions resulting from these processes are useful for incorporation into layered photoresponsive imaging devices wherein, for example, the sensitivity thereof can be varied or enhanced. These devices are thus responsive to visible light, and infrared illumination needed for laser printing, wherein gallium arsenide diode lasers are selected. Specific photoresponsive device envisioned can, for example, contain situated between a photogenerating layer and a hole transport layer, or situated between a photogenerating layer, and a supporting substrate, a photoconductive composition, comprised of the squaraine compositions prepared in accordance with the process of the present invention.

Photoconductive imaging members containing specific squaraine compositions, particularly hydroxy squaraines, are well known. Also known are layered photoresponsive devices with photogenerating layers and transport layers, reference U.S. Pat. No. 4,265,990. Examples of photogenerating layers disclosed in this patent include trigonal selenium, and phthalocyanines, while examples of transport layers that may be selected are comprised of certain diamines dispersed in an inactive resinous binder composition. Moreover, the use of certain squaraine pigments in photoresponsive imaging devices is disclosed in a copending application now U.S. Pat. No. 4,415,639, the disclosure of which is totally incorporated herein by reference, wherein there is described an improved photoresponsive device containing a substrate, a hole blocking layer, an optional adhesive interface layer, an inorganic photogenerating layer, a photoconductive composition capable of enhancing or reducing the intrinsic properties of the photogenerating layer, and a hole transport layer. As photoconductive compositions for this device, there can be selected various squaraine pigments, including hydroxy squaraine compositions of the formula as outlined on page 13, beginning at line 21 of the copending application. Additionally, there is disclosed in U.S. Pat. No. 3,824,099 certain photosensitive hydroxy squaraine compositions. According to the disclosure of this patent, the squaraine compositions are photosensitive in normal electrostatographic imaging systems.

In other copending applications, there are described the use of novel squaraine compositions of matter, such as bis-9-(8-hydroxyjulolidinyl) squaraine as imaging members. One of the imaging members contains a supporting substrate, a hole blocking layer, an optional adhesive interface layer, an inorganic photogenerating layer, a photoconducting composition layer capable of enhancing or reducing the intrinsic properties of the photogenerating layer, which compositions are comprised of the novel julolidinyl squaraine materials disclosed in the copending application, and a hole transport layer.

Also disclosed in U.S. Pat. No. 3,617,270 are optically sensitized photoconductive layers which preferably contain zinc oxide as a photoconductor, the sensitivity of which remains unchanged as a result of storage, in view of the presence of 1,3 or 1,2-squaric acid methine dyes of the formula as illustrated in column 1, beginning at line 35; while U.S. Pat. No. 3,824,099, discloses sensitive xerographic devices containing a charge generating layer comprising a squaric acid methine dye, and a charge transport layer containing a tri-arylpyrazoline compound.

Processes for preparing squaraine compositions generally involve the reaction of squaric acid with an amine. Thus, for example, the novel julolidinyl squaraine compositions disclosed in the referenced copending application are prepared by the reaction at a temperature of from about 50 degrees Centigrade to about 130 degrees Centigrade of an aromatic amine and squaric acid, in a molar ratio of from about 1.5:1 to 3:1, in the presence of a mixture of an aliphatic alcohol and an optional azeotropic cosolvent. About 200 milliliters of alcohol per 0.1 mole of squaric acid are used, while from about 40 milliliters to about 4,000 milliliters of azeotropic material are selected. Illustrative examples of amine reactants include 8-hydroxyjulolidine, while examples of aliphatic alcohols selected include 1-butanol. Azeotropic materials used include aromatic compositions such as benzene and toluene.

While the above processes for preparing squaraine compositions may be suitable for their intended purposes, there continues to be a need for other processes wherein photoconductive squaraine compositions, can be prepared. Additionally, there remains a need for simple, economical processes for preparing squaraine compositions wherein the products obtained contain impurities therein. While it is not desired to be limited by theory it is believed that the presence of impurities in the squaraine compositions resulting from the process of the present invention causes the photosensitivity of these compositions to increase. Furthermore, there continues to be a need for the preparation of squaraine compositions of enhanced photosensitivity when these compositions are selected for layered photoresponsive imaging devices. Moreover, there remains a need for processes for preparing certain squaraine compositions of enhanced photosensitivity, wherein the resulting products when incorporated into imaging members exhibit excellent dark decay and high charge acceptance values.

SUMMARY OF THE INVENTION

It is therefore an object of the present invention to provide improved processes for preparing squaraine compositions.

In another object of the present invention there are provided improved processes for preparing certain squaraine compositions, with enhanced photosensitivity, excellent dark decay properties, and acceptable charge acceptance.

In yet another object of the present invention there are provided simple, economical process for preparing squaraine compositions of enhanced photosensitivity.

In another object of the present invention, there are provided improved processes for obtaining hydroxy squaraines, julolidine squaraines, fluorinated squaraines, and other squaraine compositions.

These and other objects of the present invention are generally accomplished by providing a process for the preparation of photoconductive squaraine compositions wherein the known squaric acid reaction is accomplished in the presence of a phenol, or a squaraine phenol. In one embodiment, there is provided an improved process for the preparation of squaraine compositions which comprises reacting at an effective temperature squaric acid, an aromatic amine, and a compound selected from the group consisting of phenols, or phenol squaraines, and wherein the reaction is accomplished in the presence of an aliphatic alcohol and an optional azeotropic compound.

More specifically, the process of the present invention is illustrated with reference to the the following general and specific reactions as represented by the equations shown:

I. General Reaction

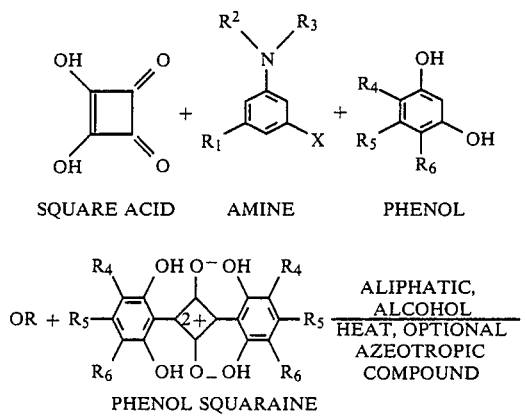

II. Specific Reaction

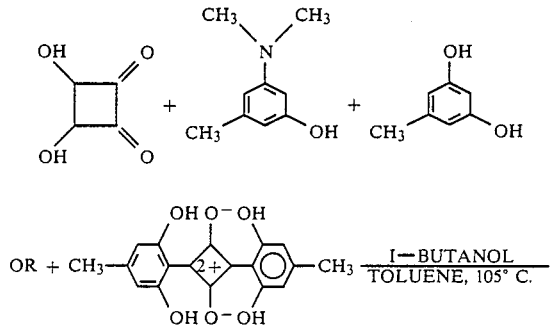

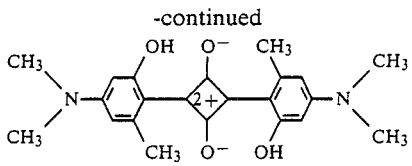

wherein $R_1$, $R_2$, $R_3$, $R_4$, $R_5$ and $R_6$ are independently selected from alkyl groups, aromatic groups and halogens, and X is hydrogen, a halogen, hydroxy, carboxy, and the like.

Illustrative examples of alkyl groups include those containing from about 1 to about 24 carbon atoms, such as methyl, ethyl, propyl, butyl, hexyl, octyl, decyl, pendecyl, and the like, with methyl, ethyl, propyl, and butyl being preferred. Examples of aromatic groups include those containing from about 6 to about 24 carbon atoms such as phenyl, naphthyl and anthryl, with phenyl being preferred. Halogens include chlorine, fluorine and bromine.

In one specific reaction sequence as illustrated herein with reference, for example, to the general and specific reaction equations, the desired squaraine compositions are prepared by suspending squaric acid in an aliphatic alcohol and an optional azeotropic substrance followed by heating. Thereafter, there is added to the resulting mixture an aromatic amine and a phenol, or a phenol squaraine with continued heating until the desired product results.

In one illustrative embodiment, the squaraine compositions of the present invention are prepared by the reaction of squaric acid and an aromatic amine, in a molar ratio of from about 1:1 to about 1:4, and preferably in a ratio of from about 1 to about 2, in the presence of a mixture of an aliphatic alcohol or a phenol, an optional azeotropic cosolvent, and a phenol, or a phenol squaraine. About 50 milliliters of alcohol per 0.02 moles of squaric acid are used, however, up to 500 milliliters of alcohol per 0.02 moles of squaric acid can be selected. Also, from about 40 milliliters to about 4,000 milliliters of azeotropic material are selected, and from about 0.004 moles to about 0.005 moles of phenol, or 0.001 moles to about 0.004 moles phenol squaraine are used. The reaction is generally accomplished at a temperature of from about 50° C. to about 130° C. and preferably at a temperature of about 105° C. with stirring until the reaction is completed. Subsequently, the desired product is isolated from the reaction mixture by known techniques such as filtration, and identified by analytical tools including NMR, mass spectroscopy, and elemental analysis for carbon, hydrogen, and nitrogen.

Examples of amine reactants include 3-dimethylamino-5-methylphenol, 3-dibutylamino-5-methylphenol, 3-diethylamino-5-methylphenol, 3-ethylmethylamino-5-methylphenol, 3-dimethylamino-5-ethylphenol, 5-dimethylamino-3-hydroxybenzoic acid, 5-ethylmethylamino-3-hydroxybenzoic acid, 3-dimethylamino-5-fluorophenol, 3-ethylmethylamino-5-fluorophenol, 3-dimethylamino-5-chlorophenol, 3-ethylmethylamino-5-chlorophenol, and the like.

While most of the amine reactants are commercially available or reported in the literature, others may be novel precursor compositions of matter, such as the aromatic amine reactant 3-butylamino-5-methylphenol. These amines are generally prepared by reacting an appropriately substituted resorcinol, such as orcinol with a secondary amine such as dimethylamine in a molar ratio of from about 1:1 to about 1:5. About one mole of water per mole of substituted resorcinol was used. Subsequently, the resorcinol and amine are heated to a temperature of about 150° C. to 200° C. in a pressure apparatus, for about 2 to about 6 hours. Any unreacted secondary amine was removed by known methods, such as evaporation, distillation or solvent extraction, and the resulting substituted amine product was isolated by known distillation or chromatography techniques. The precursor product was then identified by analytical tools including nuclear magnetic resonance, mass spectroscopy and infrared spectroscopy.

Illustrative examples of aliphatic alcohols selected for the preparation of the novel squaraines of the present invention include 1-butanol, 1-pentanol, hexanol, and 1-octanol, neopentanol, 1-heptanol, and the like, with 1-butanol being preferred, while illustrative examples of azeotropic materials that can be used include aromatic compositions such as benzene, toluene and xylene.

Illustrative examples of phenol and phenol squaraines that may be selected for the process of the present invention include orcinol, resorcinol, 2-methylresorcinol, phloroglucinol, 1,3-dihydroxynaphthalene; 2,3-dihydroxynaphthalene; 1,5-dihydroxynaphthalene; 2,7-dihydroxynaphthalene; bis(2,6-dihydroxy-4-methylphenyl)squaraine; bis(2,4,6-trihydroxyphenyl)squaraine; bis-1-(2,3-dihydroxynapthyl)squaraine; and the like.

With further regard to the molar ratio of reactants from about 0.1 moles to about 1 mole, and preferably from about 0.3 moles to about 0.4 moles of phenol, for each 0.5 moles of squaric acid are selected; while from about 0.005 moles to about 1 mole, and preferably from about 0.01 moles to about 0.02 moles of phenol squaraine composition for each 0.5 moles of squaric acid are used to effect the process of the present invention.

Illustrative examples of azeotropic materials useful as optional components for the process of the present invention include known substances such as benezene, toluene, and xylene, the primary purpose of the azeotropic substance being to remove undesirable water formed during the reaction, especially when aliphatic alcohols such as 1-butanol are selected as one of the reactants.

The reaction is accomplished at a temperature that will cause the desired products to form. Although dependant on the reactants selected, and other similar reaction parameters generally the reaction is effected at the boiling point of the aliphatic alcohol. This temperature is generally from about 68 degrees Centigrade to about 125 degrees Centigrade, and is preferably from about 99 degrees Centigrade to about 107 degrees Centigrade.

Illustrative examples of specific squaraine compositions resulting from the process of the present invention include bis(4-dimethylaminophenyl)squaraine, bis(4-diethylaminophenyl)squaraine, bis(2-fluoro-4-dimethylaminophenyl)squaraine, bis(2-fluoro-4-diethylaminophenyl)squaraine, bis(4-dimethylamino-2-hydroxy-6-methylphenyl)squaraine, bis(2-hydroxy-4-dimethylaminophenyl)squaraine, bis(2-hydroxy-4-diethylaminophenyl)squaraine, bis(2-methyl-4-dimethylaminophenyl)squaraine, and the like. The novel fluorinated squaraine compositions prepared in accordance with the process of the present invention are described in U.S. Pat. No. 4,486,520 entitled Photoconductive Devices Containing Novel Squaraine Compositions, the disclosure of which is totally incorporated herein by reference.

The resulting products subsequent to separation from the reaction mixture, by known techniques, including filtration, were identified primarily by melting point data, infrared analysis, and visible absorption spectroscopy. Additionally, the data generated from these techniques was compared with the data available for the identical compounds prepared from the known squaric acid process. Further, elemental analysis for the respective substituents, such as analysis for carbon, hydrogen, nitrogen, and fluorine was accomplished.

The squaraine compositions prepared in accordance with the process of the present invention, are useful as photoconductive substances. Thus there can be prepared a layered photoresponsive device comprised of a supporting substrate, a hole transport layer, and situated therebetween a photoconductive layer, comprised of the squaraine compositions prepared in accordance with the process of the present invention. In another embodiment, the photoresponsive device envisioned is comprised of a substrate, a photoconducting layer, comprised of the squaraine compositions prepared in accordance with the process of the present invention, and situated between the photoconducting squaraine layer, and the supporting substrate, a hole transport layer. Additionally, there can be prepared photoresponsive devices useful in printing systems wherein the imaging member is comprised of a layer of the squaraine photoconductive composition prepared in accordance with the process of the present invention, situated between a photogenerating layer, and a hole transport layer, or wherein the squaraine photoconductive squaraine composition layer is situated between a photogenerating layer, and the supporting substrate of such a device. These devices are described in U.S. Pat. No. 4,471,041 entitled Photoconductive Devices Containing Novel Squaraine Compositions, the disclosure of which is totally incorporated herein by reference.

One specific improved photoresponsive device containing therein the squaraines prepared in accordance with the process of the present invention is comprised in the order stated of (1) a supporting substrate, (2) a hole blocking layer, (3) an optional adhesive interface layer, (4) an inorganic photogenerator layer, (5) a photoconductive composition layer capable of enhancing or reducing the intrinsic properties of the photogenerating layer, which composition is comprised of the squaraine materials prepared in accordance with the process of the present invention, and (6) a hole transport layer.

The photoresponsive devices described can be prepared by a number of known methods, reference for example the copending applications indicated, the process parameters and the order of coating of the layers being dependent on the device desired. Thus, for example, a three layered photoresponsive device can be prepared by vacuum sublimation of the photoconducting layer on a supporting substrate, and subsequently depositing by solution coating the hole transport layer. In another process variant, the layered photoresponsive device can be prepared by providing the conductive substrate containing a hole blocking layer and an optional adhesive layer, and applying thereto by solvent coating processes, laminating processes, or other methods, a photogenerating layer, a photoconductive composition comprised of the squaraines of the present invention, which squaraines are capable of enhancing or reducing the intrinsic properties of the photogenerating layer in the infrared and/or visible range of the spectrum, and a hole transport layer.

The improved photoresponsive devices of the present invention can be incorporated into various known imaging systems, including xerographic imaging processes. Additionally, the improved photoresponsive devices of the present invention containing an inorganic photogenerating layer, and a photoconductive layer comprised of the squaraines prepared in accordance with the process of the present invention can function simultaneously in imaging and printing systems with visible light and/or infrared light. In this embodiment, the improved photoresponsive devices of the present invention may be negatively charged, exposed to light in a wavelength of from about 400 to about 1,000 nanometers, either sequentially or simultaneously, followed by developing the resulting image and transferring to paper.

The invention will now be described in detail with reference to specific preferred embodiments thereof, it being understood that these examples are intended to illustrative only. The invention is not intended to be limited to the materials, conditions, or process parameters recited herein, it being noted that all parts and percentages are by weight unless otherwise indicated.

EXAMPLE I

Preparation of control
bis(4-dimethylamino-2-hydroxy-6-methylphenyl)-squaraine

A 300 milliliter three-necked flask equipped with a Dean-Stark trap and reflux condenser was charged with squaric acid, 2.3 grams, 0.02 mol., n-butanol, 110 milliliters and toluene, 120 milliliters, followed by heating to 105° C. At a temperature of about 95° C., the squaric acid began to dissolve. When dissolution was complete, about 35 minutes, 3-dimethylamino-5-methylphenol, 6.0 grams, 0.04 mol. was added in one portion and the reaction temperature was maintained at 105° C. until completion, about 3 hours. On addition of the 3-dimethylamino-5-methylphenol, the colorless reaction mixture changed to a deep green. In 30 minutes when 0.1 milliliters of water had collected in the Dean-Stark trap, crystals began collecting at the bottom of the flask. After 3 hours, 0.6 milliliters of water had collected in the Dean-Stark trap at which time the reaction was stopped by collecting the crystals on a Millipore LC 10 micron filter. The crystals were washed with three, 50 milliliter portions of ethyl acetate.

The metallic green crystals which had a decomposition point of 297° C., were identified as bis(4-dimethylamino-2-hydroxy-6-methylphenyl)squaraine, (5.9 grams, 77% yield) by mass spectroscopy, proton nuclear magnetic resonance, infrared and chemical analysis.

By decomposition at 297° C. is meant that the crystals discolored from green to black when achieving this temperature. Additionally, infrared analysis of the squaraine obtained indicated an absorption band at 1612 cm$^{-1}$, as a KBr pellet. The mass spectrum showed a molecular ion at 380 daltons. The proton magnetic resonance spectrum showed proton signals at 2.69, 3.12, 5.98, 6.19 and 13.35 ppm.

The product provided a visible absorption band in methylene chloride at 660 nanometers with a log of the extinction coefficient of 5.36.

Chemical Analysis for $C_{22}H_{24}N_2O_4$

| Element | Theoretical | Found |
| --- | --- | --- |
| C | 69.46% | 70.05% |
| H | 6.36% | 6.45% |
| N | 7.36% | 7.49% |

EXAMPLE II

Preparation of
Bis(4-dimethylamino-2-hydroxy-6-methylphenyl)-squaraine Compositions in the presence of variable orcinol concentrations For each squaraine composition prepared a 200 milliliter three-necked flask equipped with a Dean-Stark trap and a reflux condenser was charged with squaric acid, 2.8 grams, 0.025 mol., n-butanol, 100 milliliters and toluene, 60 milliliters. The reaction mixture was then heated to 105° C. At a temperature of about 95° C. squaric acid began to dissolve. When dissolution was complete, about 35 minutes, 3-dimethylamino-5-methylphenol, 7.4 grams, 0.049 mol. was added in one portion as a powder followed by the addition of orcinol monohydrate, in the amounts reported in Table I that follows. The reaction temperature was maintained at 105° until completion about 4 hours. On addition of the 3-dimethylamino-5-methyl-phenol, the colorless reaction mixture changed to a deep green. As the reaction progressed the color of the reaction mixture changed from deep green to blue. In 20 minutes 0.7 milliliters of water had collected in the Dean-Stark trap. After 4 hours 1.2 milliliters had collected in the Dean-Stark trap, at which time the reaction was stopped by collecting the crystals on a Millipore LC 10 micron filter.

The resulting metallic green crystals were then washed with 3, 50 milliliter portions of ethyl acetate, and identified as bis(4-dimethylamino-2-hydroxy-6-methylphenyl)squaraine by infrared, UV, and x-ray powder diffraction.

TABLE I

|   | Grams Orcinol | Mols Orcinol | Mol % Orcinol |
| --- | --- | --- | --- |
| 1 | 0.182 | 0.0015 | 3 |
| 2 | 0.608 | 0.0049 | 10 |
| 3 | 1.095 | 0.0088 | 18 |
| 4 | 1.216 | 0.0098 | 20 |
| 5 | 2.311 | 0.0186 | 38 |
| 6 | 3.528 | 0.0284 | 58 |
| 7 | 4.745 | 0.0382 | 78 |
| 8 | 5.961 | 0.0480 | 98 |

Accordingly, in accordance with the processes illustrated in this example, eight squaraine compositions were prepared, all of which were identified as bis(4-dimethylamino-2-hydroxy-6-methylphenyl)squaraine as indicated herein.

EXAMPLE III

Preparation of Hydroxy Methyl Squaraine in the presence of resorcinol

A 200 milliliter three-necked flask equipped with a Dean-Stark trap and a reflux condenser was charged with squaric acid, 2.8 grams, 0.025 mol., n-butanol, 100 milliliters and toluene, 60 milliliters. The reaction mixture was then heated to 105° C. At a temperature of about 95° C. squaric acid began to dissolve. When dissolution was complete, about 35 minutes, 3-dimethylamino-5-methylphenol, 7.4 grams, 0.049 mol. was added in one portion as a powder followed by the addition of rescorinol 1.618 grams, 0.0147 mol. The reaction temperature was maintained at 105° until completion, about 4 hours. On addition of the 3-dimethylamino-5-methylphenol, the colorless reaction mixture changed to a deep green. Later as the reaction progressed the color of the reaction mixture changed from deep green to blue. In 20 minutes 0.7 milliliters of water had collected in the Dean-Stark trap. After 4 hours 1.2 milliliters of water had collected in the Dean-Stark trap, at which time the reaction was stopped. The product crystals were then collected on a Millipore LC 10 micron filter.

The crystals metallic green in color were washed with 3, 50 milliliter portions of ethyl acetate, and identified as bis(4-dimethylamino-2-hydroxy-6-methylphenyl)squaraine by infrared analysis and nuclear magnetic resonance analysis.

EXAMPLE IV

Preparation of bis(4-dimethylamino-2-hydroxy-6-methylphenyl)-squaraine in the presence of phloroglucinol A 200 milliliter three-necked flask equipped with a Dean-Stark trap and a reflux condenser was charged with squaric acid, 2.8 grams, 0.025 mol., n-butanol, 100 milliliters and toluene, 60 milliliters. The reaction mixture was then heated to 105° C. At a temperature of about 95° C. squaric acid began to dissolve. When dissolution was complete, about 35 minutes, 3-dimethylamino-5-methylphenol, 7.4 grams, 0.049 mol. was added in one portion as a powder followed by the addition of phloroglucinol dihydrate, 2.38 grams, 0.0147 mol. The temperature was maintained at 105° until the reaction was complete, about 4 hours. On addition of the 3-dimethylamino-5-methylphenol, the colorless reaction mixture changed to a deep green. Later as the reaction progressed the color of the reaction mixture changed from deep green to blue. In 20 minutes 0.7 milliliters of water had collected in the Dean-Stark trap. After 4 hours 1.2 milliliters had collected in the Dean-Stark trap, at which time the reaction was stopped. There was then collected the product on a Millipore LC 10 micron filter.

These crystals, metallic green in color were washed with 3, 50 milliliter portions of ethyl acetate, and identified as bis(4-dimethylamino-2-hydroxy-6-methylphenyl)squaraine by infrared analysis and nuclear magnetic resonance analysis.

EXAMPLE V

Preparation of bis(4-dimethylamino-2-hydroxy-6-methylphenyl)-squaraine in the presence of bis(2,6-dihydroxy-4-methylphenyl)squaraine A 200 milliliter three-necked flask equipped with a Dean-Stark trap and a reflux condenser was charged with squaric acid, 2.8 grams, 0.025 mol., n-butanol, 100 milliliters and toluene, 60 milliliters. The reaction nmixture was then heated to 105° C. At a temperature of about 95° C. squaric acid began to dissolve. When dissolution was complete, about 35 minutes, 3-dimethylamino-5-methylphenol, 7.4 grams, 0.049 mol. was added in one portion as a powder followed by the addition of bis(2,6-dihydroxy-4-methylphenyl)squaraine, 0.158 grams, 0.0005 mol. The temperature was maintained at 105° until the reaction was complete, about 4 hours. On addition of the 3-dimethylamino-5-methylphenol, the colorless reaction mixture changed to a deep green. Later as the reaction progressed the color of the reaction mixture changed from deep green to blue. In 20 minutes 0.7 milliliters of water had collected in the Dean-Stark trap. After 4 hours 1.2 milliliters had collected in the Dean-Stark trap, at which time the reaction was stopped. The crystal product was collected on a Milliport LC 10 micron filter.

The resulting crystals were washed three times with ethyl acetate. These metallic green crystals were identified as bis(4-dimethylamino-2-hydroxy-6-methylphenyl)squaraine by infrared analysis and nuclear magnetic resonance analysis resulting in substantially identical data as reported in Example I.

EXAMPLE VI

Preparation of Bis(2,6-Dihydroxy-4-methylphenyl)squaraine of Example V

In a 200 milliliter three-necked flask equipped with a Dean-Stark trap and a reflux condenser was charged with squaric acid, 3.44 grams, 0.0302 mol., octanol, 75 milliliters and toluene, 75 milliliters. The reaction mixture was then heated to 120° C. At a temperature of about 95° C. squaric acid began to dissolve. When dissolution was complete, about 30 minutes, orcinol monohydrate, 8.85 grams, 0.0622 mol. was added in one portion. The temperature was maintained at 120° until the reaction was complete, (2.5 hours). The crystalline product was isolated by filtration and these crystals were subsequently washed with 4 portions of hexane, 15 milliliters. The purple crystals were identified as bis(2,6-dihydroxy-4-methylphenyl)squaraine, 1.93 grams, yield 20 percent, by visible absorption spectroscopy and nuclear magnetic resonance.

The visible absorption band in dichloromethane appears at 562 nanometers with an extinction coefficient of 88,500. The proton nuclear magnetic resonance clearly identifies this compound as bis(2,6-dihydroxy-4-methylphenyl)squaraine as opposed to the bis(2,4-dihydroxy-6-methylphenyl)squaraine. For example, the methyl group appears as a triplet ($^4J_{HH}=0.55+0.5$ Hz) consistent only with the bis(2,6-dihydroxy-4-methylphenyl)squaraine. Proton nuclear magnetic resonance peaks in deuterated dichloromethane appear at 2.295, 6.263 and 11.089 parts per million.

EXAMPLE VII

Preparation of Control Methyl Squaraine Composition

A 500 milliliter, three-necked flask, equipped with a Dean-Stark trap and reflux condensor was charged with squaric acid, 4.56 grams, 0.04 mol., n-butanol, 150 milliliters and toluene, 150 milliliters. The reaction mixture was then heated to 105°. At a temperature of about 95°, squaric acid began to dissolve. When dissolution was two-thirds complete, about 15 minutes, N-N-dimethyl-m-toluidine, 10.7 grams, 0.08 mole was added on one portion. The reaction mixture was heated 6.5 hours at reflux and the product was isolated by filtration through a Millipore LC 10 micron filter. The resulting crystals were washed with 3, 50 milliliter portions of ethyl acetate. The metallic green crystals which had a decomposition point of 249° C., were identified as bis(4-dimethylamino-2-methylphenyl)squaraine, 5.5 grams, 40 percent yield by infrared, nuclear magnetic resonance and chemical analysis. By decomposition at 249° C. is meant that the crystals discolored from green to black when achieving this temperature. Additionally, infrared analysis of the squaraine obtained indicated an absorption band at 1595 cm$^{-1}$, as a KBr pellet.

The x-ray powder diffraction spectrum showed bands at two theta values of 10.8, 11.4, 13.4, 21.8, 22.8, 25.8 and 26.4. The proton nuclear magnetic resonance spectrum taken in deuterochloroform and benzene -$d_6$ showed absorption bands at 2.69, 2.99 and 6.3–6.7 parts per million.

Chemical analysis for $C_{22}H_{24}N_2O_7$

| Element | Theoretical | Found |
|---------|-------------|-------|
| C       | 75.83       | 75.79 |
| H       | 6.94        | 7.18  |
| N       | 8.03        | 8.07  |

EXAMPLE VIII

Preparation of MethylSquaraine in the presence of Orcinol

A 500 milliliter, three-necked flask, equipped with a Dean-Stark trap and reflux condenser was charged with squaric acid, 4.56 grams, 0.04 mol., n-butanol, 150 milliliters and toluene, 150 milliliters. The reaction mixture was then heated to 105° C. At a temperature of about 95° C., squaric acid began to dissolve. When dissolution was two-thirds complete, about 15 minutes, orcinol monohydrate, 3.41 grams, 0.024 moles was added in one portion followed immediately by the addition of 10.7 grams, 0.08 moles N-N-dimethyl-m-toluidine. The reaction mixture was heated for 6.5 hours at reflux and the product was isolated by filtration through a Millipore LC 10 micron filter. The resulting crystals were washed with 3, 50 milliliter portions of ethyl acetate. The product, identified in accordance with the procedure of Example VII, consisted predominantly of bis(4-dimethylamino-2-methylphenyl)squaraine 1.9 grams, 13 percent yield.

EXAMPLE IX

Preparation of Methyl Squaraine in the presence of bis(2,6-dihydroxy-4-methylphenyl)squaraine A 500 milliliter, three-necked flask, equipped with a Dean-Stark trap and reflux condenser was charged with squaric acid, 4.56 grams, 0.04 mol., n-butanol, 150 milliliters and toluene, 150 milliliters. The reaction mixture was heated to 105°. At a temperature of about 95°, squaric acid began to dissolve. When dissolution was two-thirds complete, about 15 minutes, bis(2,6-dihydroxy-4-methylphenyl)squaraine, 0.234 grams, 0.0007 moles was added in one portion immediately followed by the addition of 10.7 grams, 0.08 moles of N-N-dimethyl-m-toluidine. The reaction mixture was heated 6.5 hours at reflux and the product was isolated by filtration through a Millipore LC 10 micron filter. The resulting crystals were washed with 3, 50 milliliter portions ethyl acetate. The product, identified in accordance with the procedure of Example VII, consisted predominantly of bis(4-dimethylamino-2-methylphenyl)squaraine 6.8 grams, 49 percent yield.

EXAMPLE X

Preparation of photoresponsive devices incorporating HydroxyMethyl Squaraine Compositions Photoresponsive devices were prepared with the squaraine compositions as prepared in Examples I to V by providing in each instance an aluminized Mylar ® substrate, of a thickness of 3 mils, followed by applying thereto with a multiple clearance film applicator in a wet thickness of 0.5 mils, a layer of 3-aminopropyltrimethoxysilane available from PCR Research Chemicals, Florida, in ethanol in a 1:50 volume ratio. This layer was then allowed to dry for 5 minutes at 110° C. in a forced air oven. Photoconductive layers containing 30 percent by weight of bis(4-dimethylamino-2-hydroxy-6-methylphenyl)squaraine synthesized as described in Examples 1–5 was then prepared as follows:

In a separate 2 ounce amber bottle, there were added 0.33 grams of the respective squaraines, 0.77 grams of Vitel PE-200 ®, a polyester available from Goodyear, 70 grams of ⅛" stainless steel shot, and 16.34 grams of methylethyl ketone solvent mixture in a 4:1 volume ratio. The above mixture was placed on a ball mill for 24 hours. The resulting slurry was then coated on the above prepared aluminized Mylar ® substrate, which had been overcoated with the silane layer, with a multiple clearance film applicator, to a wet thickness of 1 mil. This layer was allowed to air dry for 5 minutes. The resulting device was dried at 135° C. for 6 minutes in a forced air oven. The dry thickness of the squaraine layer was 1 micron.

The above photoconductive layers in each instance were then overcoated with a charge transport layer, which was prepared as follows:

A transport layer composed of 50 percent by weight Makrolon ®, a polycarbonate resin available from Larbensabricken Bayer A. G. was mixed with 50 percent by weight N,N-diphenyl'-bis(3-methylphenyl)-1,1'-biphenyl-4,4'-diamine. This solution was mixed to 9 percent by weight in methylene chloride. All of these components were placed in an amber bottle and dissolved. The mixture was coated to give a layer with a dry thickness of 30 microns on top of the above photoconductive layer, using a multiple clearance film applicator of 15 mils wet gap thickness. The resulting device was then air dried at room temperature for 20 minutes and then in a forced air oven at 135° C. for 6 minutes.

EXAMPLE XI

Preparation of photoresponsive devices incorporating Methyl Squaraine

Photoresponsive devices were prepared with the squaraine compositions as prepared in Examples VII to IX by providing in each instance an aluminized Mylar ® substrate, of a thickness of 3 mils, followed by applying thereto with a multiple clearance film applicator in a wet thickness of 0.5 mils, a layer of 3-aminopropyltrimethoxysilane available from PCR Research Chemicals, Florida, in ethanol in a 1:50 volume ratio. This layer was then allowed to dry for 5 minutes at 110° C. in a forced air oven. Photoconductive layers containing 30 percent by weight of bis(4-dimethylamino-2-methylphenyl)squaraine synthesized as described in Examples VII–IX was then prepared as follows:

In a separate 2 ounce amber bottle, there was added 0.33 grams of the respective squaraines, 0.77 grams of Vitel PE-200 ®, a polyester available from Goodyear, 70 grams of ⅛" stainless steel shot, and 16.34 grams of methylethyl ketone solvent mixture in a 4:1 volume ratio. The above mixture was placed on a ball mill for 24 hours. The resulting slurry was then coated on the above prepared aluminized Mylar ® substrate which had been overcoated with the silane layer, with a multiple clearance film applicator, to a wet thickness of 1 mil. This layer was allowed to air dry for 5 minutes. The resulting device was dried at 135° C. for 6 minutes in a forced air oven. The dry thickness of the squaraine layer was 0.6 micron.

The above photoconductive layers in each instance were then overcoated with a charge transport layer, which was prepared as follows:

A transport layer composed of 50 percent by weight Makrolon ®, a polycarbonate resin available from Larbensabricken Bayer A. G. was mixed with 50 percent by weight N,N'-diphenyl-bis(3-methylphenyl)-1,1'-biphenyl-4,4'-diamine. This solution was mixed to 9 percent by weight in methylene chloride. All of these components were placed in an amber bottle and dissolved. The mixture was coated to give a layer with a dry thickness of 30 microns on top of the generator layer, using a multiple clearance film applicator of 15 mils wet gap thickness. The resulting device was then air dried at room temperature for 20 minutes and then in a forced air oven at 135° C. for 6 minutes.

EXAMPLE XII

Xerographic evaluation of photoresponsive devices as prepared in Example X, XI

The photoresponsive devices as prepared in Examples X and XI were then tested for photosensitivity in the visible and infrared region of the spectrum by negatively charging with a corotron to −950 volts followed by simultaneously exposing each device to monochromatic light in a wavelength region of from about 400 to 1,000 nanometers. The surface potential of each device was then measured with an electrical probe after exposure to given wavelengths. The percent discharge of each device was then calculated as disclosed hereinbefore, which percent discharge indicates photoresponse.

The devices of Example X had sufficient discharge so as to respond to light in a wavelength range of from about 400 to 950 nanometers, indicating both visible and infrared photosensitivity for these devices.

Also the photoresponsive devices as prepared in Example XI were tested for photosensitivity by charging each of the devices in the dark to a surface potential of −950 volts, followed by measuring with an electrical probe the amount of light energy of monochromatic light of 830 nanometers supplied by a Xenon lamp, in ergs per centimeter squared required to discharge each device to one half of its surface potential. A low discharge number, (i.e. $E_{\frac{1}{2}}$) for example below 100, indicates excellent photosensivity for the devices involved.

Table II summarizes $E_{\frac{1}{2}}$ values (i.e. discharge numbers) for the photoresponsive devices, described in Example X containing hydroxy methyl squaraine synthesized in the presence of various phenol and phenol squaraine additives. This data shows that significant improvements in the photosensitivity of hydroxymethyl squaraine can be achieved with the phenol additives indicated. Discharge numbers decrease from 60 ergs/cm² for the control to 10 ergs/cm² with orcinol. This demonstrates the photosensitivity enhancement obtained with orcinol.

The photosensitivity enhancement is also demonstrated when resorcinol, phloroglucinol and bis(2,6-dihydroxy-4-methylphenyl)squaraine are added during the synthesis of bis(4-dimethylamino-2-hydroxy-6-methylphenyl)squaraine. Reduced photodischarge numbers of 10, 28 and 16 ergs/cm² are observed respectively, compared to 60 ergs/cm² for the control.

TABLE II

Photosensitivity of Photoresponsive Devices Containing Hydroxy Methyl Squaraine

| Synthesis described in Example No. | Additive Added | Mole % | Photodischarge No. $E_{\frac{1}{2}}$ (ergs/cm²) |
|---|---|---|---|
| I. (control) | None | 0 | 60 |
| II. | Orcinol | 3 | 37 |
| | | 10 | 21 |
| | | 18 | 14 |
| | | 20 | 11 |
| | | 38 | 10 |
| | | 58 | 10 |
| | | 78 | 10 |
| | | 98 | 9 |
| III. | Resorcinol | 30 | 10 |
| IV. | Phloroglucinol | 30 | 28 |
| V. | Bis(2,6-dihydroxy-4-methylphenyl)squaraine | 1.1 | 16 |

EXAMPLE XIII

The photoresponsive devices as prepared in Example XI were then tested for photosensitivity as described in Example XII.

Table III summarizes photodischarge numbers i.e. $E_{\frac{1}{2}}$, for the photoresponsive devices described in Example XI, containing bis(4-dimethylamino-2-methylphenyl)squaraine synthesized in the presence of phenol and phenol squaraine additives.

This data indicates significant improvement in the photosensitivity of bis(4-dimethylamino-2-methylphenyl)squaraine when orcinol or orcinol squaraine is added to the reaction mixture as compared to the control methyl squaraine when no additives are used. The reduced photodischarge numbers are 32 are 24 ergs/cm² respectively, compared to 43 ergs/cm² for the control.

TABLE III

Photosensitivity of Photoresponsive Devices Containing Methyl Squaraine

| Synthesis described in Example No. | Additive | Mole % Added | Photodischarge No. $E_{\frac{1}{2}}$ (ergs/cm²) |
|---|---|---|---|
| VII. (control) | None | 0 | 43 |
| VIII. | Orcinol | 30 | 32 |
| IX. | Bis(2,6-dihydroxy-4-methyl phenyl)squaraine | 2 | 24 |

Although the invention has been described with reference to specific preferred embodiments, it is not intended to be limited thereto, rather those skilled in the art will recognize that variations and modifications may be made therein which are within the spirit of the present invention and within the scope of the following claims.

We claim:

1. An improved process for the preparation of squaraine compositions which comprises reacting squaric acid, an aromatic amine, and a composition selected from the group consisting of phenols and phenol squaraines, in the presence of an aliphatic alcohol, and an optional azeotropic substance.

2. An improved process in accordance with claim 1 wherein the reaction is accomplished at a temperature of from about 65° C. to about 130° C.

3. A process in accordance with claim 1 wherein the phenol is orcinol.

4. A process in accordance with claim 1 wherein the phenol is resorcinol.

5. A process in accordance with claim 1 wherein the phenol is phloroglucinol.

6. A process in accordance with claim 1 wherein the phenol squaraine is bis(2,6-dihydroxy-4-methylphenyl)squaraine.

7. A process in accordance with claim 1 wherein the aliphatic alcohol contains from about 1 carbon atom to about 6 carbon atoms.

8. A process in accordance with claim 1 wherein the alcohol is butanol.

9. A process in accordance in claim 1 wherein the alcohol is heptanol.

10. A process in accordance with claim 1 wherein the amine reactant is 3-dimethylamino-5-methylphenyl.

11. A process in accordance with claim 1 wherein the amine reactant is N,N-dimethyl-m-toluidine.

12. A process in accordance with claim 1 wherein there results the product bis(4-dimethylaminophenyl)squaraine.

13. A process in accordance with claim 1 wherein there results bis(2-fluoro-4-dimethylaminophenyl)squaraine.

14. A process for the preparation of squaraine compositions which comprises reacting at a temperature of from about 65° C. to about 130° C. squaric acid, an aromatic amine composition I, a phenol II, or a phenol squaraine III, which reaction is effected in the presence of an aliphatic alcohol, and an azeotropic substance, wherein $R_1$, $R_2$, $R_3$, $R_4$, $R_5$, and $R_6$ are independently selected from aromatic groups, alkyl groups, and halogens, and X is hydrogen, halogen, hydroxy, or carboxy.

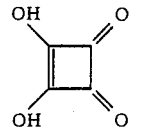

I.

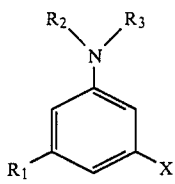

II.

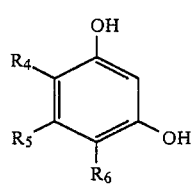

III.

15. A process in accordance with claim 14 wherein x is a hydroxy.

16. A process in accordance with claim 14 wherein x is fluorine.

17. A process in accordance with claim 14 wherein the aliphatic alcohol is 1-butanol.

18. A process in accordance with claim 14 wherein the azeotropic substance is toluene or benzene.

19. A process in accordance with claim 14 wherein the alkyl groups contain from about 1 carbon atom to about 6 carbon atoms.

20. A process in accordance with claim 14 wherein the aromatic group is phenyl.

21. A process in accordance with claim 14 wherein the phenol is orcinol.

22. A process in accordance with claim 14 wherein the phenol is resorcinol.

23. A process in accordance with claim 14 wherein the phenol is phlorglucinol.

24. A process in accordance with claim 14 wherein the phenol squaraine is bis(2,6-dihydroxy-4-methylphenyl)squaraine.

25. A process in accordance with claim 14 wherein the squaraine resulting is bis(4-dimethylaminophenyl)squaraine.

26. A process in accordance with claim 14 wherein the squaraine resulting is bis(2-fluoro-4-dimethylaminophenyl)squaraine.

* * * * *